(12) United States Patent
Schliwa-Bertling et al.

(10) Patent No.: US 8,200,215 B2
(45) Date of Patent: Jun. 12, 2012

(54) CODEC RATE ADAPTATION FOR RADIO CHANNEL RATE CHANGE

(75) Inventors: Paul Schliwa-Bertling, Ljungsbro (SE); Per-Ove Ekman, Sturefors (SE)

(73) Assignee: Telefonaktiebolaget LM Ericsson (publ), Stockholm (SE)

(*) Notice: Subject to any disclaimer, the term of this patent is extended or adjusted under 35 U.S.C. 154(b) by 401 days.

(21) Appl. No.: 12/607,404

(22) Filed: Oct. 28, 2009

(65) Prior Publication Data

US 2012/0028642 A1    Feb. 2, 2012

(51) Int. Cl.
*H04Q 7/20* (2006.01)

(52) U.S. Cl. ........... 455/432.2; 455/200.1; 455/552.1; 704/500; 370/356

(58) Field of Classification Search .......... 455/450–453, 455/446–447, 464, 436–444, 456.5, 33.2, 455/561, 432.2; 370/336–337, 329–331, 370/319–326, 314, 343–345, 356; 704/500
See application file for complete search history.

(56) References Cited

U.S. PATENT DOCUMENTS

| | | | |
|---|---|---|---|
| 7,181,209 B2 * | 2/2007 | Tamura ............... | 455/432.1 |
| 7,403,892 B2 | 7/2008 | Sjoberg et al. | |
| 7,500,018 B2 * | 3/2009 | Hakansson et al. ........ | 709/246 |
| 7,639,727 B1 * | 12/2009 | Brisebois et al. ........ | 375/134 |
| 7,778,272 B2 * | 8/2010 | Holma ..................... | 370/465 |
| 2004/0267519 A1 * | 12/2004 | Sjoberg et al. ............ | 704/201 |
| 2005/0055203 A1 * | 3/2005 | Makinen et al. .......... | 704/229 |
| 2005/0102136 A1 * | 5/2005 | Makinen et al. .......... | 704/214 |
| 2006/0281485 A1 * | 12/2006 | Johnson et al. .......... | 455/552.1 |
| 2008/0133247 A1 * | 6/2008 | Kurittu ................... | 704/500 |
| 2008/0212575 A1 * | 9/2008 | Westberg ............... | 370/356 |

FOREIGN PATENT DOCUMENTS

| | | |
|---|---|---|
| EP | 1 739 989 A1 | 1/2007 |
| WO | WO 2006/135334 A2 | 12/2006 |
| WO | WO 2007/121163 A1 | 10/2007 |
| WO | WO 2009/090582 A1 | 7/2009 |

OTHER PUBLICATIONS

Written Opinion of the International Search Authority and International Search Report mailed Jan. 28, 2011 in corresponding Application No. PCT/SE2010/051065.
3GPP TS 26.071 V8.0.0 (Dec. 2008), pp. 1-12.

* cited by examiner

*Primary Examiner* — Kent Chang
*Assistant Examiner* — Keith Fang
(74) *Attorney, Agent, or Firm* — Nixon & Vanderhye P.C.

(57) ABSTRACT

Speech signals to be sent between a first node and a second node via a wireless communication system are Adaptive Multi-Rate (AMR) encoded. A need to change the first node's first data transmission rate over a radio interface to a second different data transmission rate is determined. A new AMR source bit rate is then determined for both nodes. Information is sent to the second node, in advance of changing the data transmission rate over the radio interface, requesting the second node to change towards the new AMR source bit rate. After a predetermined time period sufficient for the second node to change from the current AMR source bit rate to the new AMR source bit rate expires or after the second node indicates a change to the new AMR source bit rate, the first node starts transmitting at the second data transmission rate over the radio interface.

33 Claims, 16 Drawing Sheets

CODEC RATE ADAPTATION FOR RADIO CHANNEL RATE CHANGE

TECHNICAL FIELD

The technical field relates to mobile radio communications, and in particular, to adapting codec rates when a radio channel rate change is needed.

BACKGROUND

Recently, Internet Protocol (IP) transport solutions have been considered for 3rd generation (3G) mobile communications networks because of the flexibility and wide deployment of IP technologies. For example, the 3GPP release 8 intends to support user plane over the A interface between the radio access network and the core network using IP (AoIP) protocol [3GPP TS 48.008] and AoIP userplane transport mechanism [3GPP TS 48,103]. AoIP permits the situation where transcoder equipment may only be located in the core network (e.g., a mobile gateway (MGw)), in which case, transcoder resources are not available in the radio access network. An advantage of AoIP is the possibility and high probability to conduct a speech call in a Transcoder Free Operation mode (TrFO). AoIP together with an adaptive voice coding, e.g., Adaptive Multi-Rate Narrowband (AMR-NB), and with the ability to operate over a wide range of voice codec bit rates can use a GSM radio network with full rate and half rate traffic channels to its full potential.

Adaptive voice coding; e.g., Adaptive Multi-Rate (AMR), can be used to vary the bit rate of voice codecs for different reasons, e.g. to adapt to radio quality, to adapt to the load situation in the network, and to adapt to the width of local and remote radio interfaces. The protocol enhancements for AoIP mentioned above ensure that end-to-end codec negotiation takes place at the initial call set-up between a local mobile radio node and a remote radio node, and that a TrFO mode is maintained even when a handover is required because a mobile radio node moves or when Radio Resource Management (RRM) in the radio network must adapt codec rates in mobile radio nodes to accommodate current radio conditions and/or a current radio resource situation. If the RRM output requires a change of an ongoing TrFO call to a codec that is incompatible with that currently used, e.g., GSM_FR (full rate) to GSM_HR (half rate) or AMR-NB to GSM_EFR, then a transcoder resource must be inserted to convert between these two different codec types. In 3GPP TS 48.008, the procedure to insert such transcoder resource is called Internal BSS (Base Station Subsystem) Handover with MSC (Mobile Switching Center) support. But if the call operates using AMR codecs and the output of RRM indicates a change of traffic channel bit rate (e.g., from full rate to half rate) for an AMR-NB call, then a change to a compatible codec is assumed, which means that no transcoder resource is required, and the change is handled by BSS without support from MSC. As a result, the call can be kept in a TrFO mode.

Because the codec set used for AMR-NB on a full rate traffic channel and the codec set used for AMR-NB on a half rate traffic channel are compatible (from the decoder point of view), and thus no transcoder equipment is required when a rate/mode change occurs, there is no need for explicit control signaling to the core network or to the remote mobile radio node when a change from one to another occurs. With both ends configured with compatible codec sets, the lower codec modes for both are the same. However, the source rate of the payload generated by an AMR in the FR case with good radio conditions will not "fit" into a radio channel on the radio interface configured for AMR half rate channel. In other words, AMR codec modes with bitrates above 7.40 kbps corresponding to AMR on a full rate traffic channel with good radio conditions do not fit on a half rate radio channel which only accommodates 7.40 kbps or less.

A problem thus occurs when the traffic channel for the local mobile radio node, for example, is changed from full rate (FR) to half rate (HR) during a call with the remote mobile radio node. The local mobile radio node starts operating at a low codec mode, known as initial codec mode, and the remote mobile radio node only adapts to the new rate after it has received the information in an AMR codec mode request (CMR) message embedded in a the AMR payload from the local mobile radio node. The CMR message is the mechanism where the receiver node tells the sender node which codec modes that are the highest possible for the last step to the receiver. Consequently, the adaptation takes at least one round-trip-delay between the local mobile radio node and the remote mobile radio node, i.e., approximately 300-400 ins, starting from when the local mobile radio node has set-up the new radio channel which in the example above is when the local mobile radio node has changed from a traffic channel configured for full rate to a traffic channel configured for half rate. All the AMR frames from the remote mobile radio node to be transmitted to the local mobile radio node over the radio interface during this time will be discarded at the radio interface until the remote mobile radio node adapts its codec rate from a codec rate above what can be transmitted on a half rate traffic channel down to a codec rate that "fits" the half rate channel. As a result, the user at the local node detects audible distortion or dropouts and experiences overall decreased speech quality.

The same problem appears for an inter-BSS Handover. For example, the new local mobile radio node and the new base station may start with a low codec mode on a half rate radio channel after the inter-BSS Handover, while the remote mobile radio node might still be using a high codec mode on a full rate radio channel until the remote node is informed of the rate change.

SUMMARY

Speech signals are to be sent between a first node and a second node in a wireless communication system. An adaptive multi-rate (AMR) encoder associated with each of the first and second nodes encodes speech signals in multiple modes having different degrees of robustness that correspond to different AMR source bit rates. For a communication established between the first node and the second node, the first node transmits over a radio interface at a first data transmission rate, and the AMR encoders associated with the first and second nodes generate source data for transmission at a first AMR source bit rate. A need to change the first node's first data transmission rate over the radio interface to a second different data transmission rate is determined. In response to the determined need, a new AMR source bit rate is determined for the first and second nodes. Information is sent to the second node, in advance of changing the data transmission rate over the radio interface, requesting the second node to change from its currently used AMR source bit rate towards the new AMR source bit rate. After a predetermined time period sufficient for the second node to change from the current AMR source bit rate to the new AMR source bit rate expires or after the second node indicates a change to the new AMR source bit rate, an indication is sent to the first node to start transmitting at the second data transmission rate over the radio interface.

In one non-limiting, example embodiment, the predetermined delay period is waited for before performing the sending step to allow sufficient time for the second node to adjust its AMR source encoding rate to the second AMR source encoding rate. In this way, the AMR source encoding rate of information sent to first node is compatible with the second data transmission rate over the radio interface.

One non-limiting aspect of the technology includes sending information to the second node using in-band signaling in a user plane and that information is a codec mode request or command.

Another non-limiting aspect of the technology may include detecting a condition that indicates a need to change the first node's first data transmission rate over the radio interface.

One example, non-limiting application is to a GSM-based wireless communication system. If a congestion condition is detected, the change may be from a full rate radio channel and to a half rate radio channel. The information sent to the second node may be a codec mode request or command, and the current AMR source rate may correspond to a full rate AMR mode and the codec mode request or command corresponds to a half rate AMR mode. In response to the determined need, a timer set with a predetermined delay period may be started, and after the timer expires, an indication may be sent to the first node to start transmitting at the half rate data transmission rate over the radio interface. Waiting for the predetermined delay period before performing the commanding step allows sufficient time for the second node to adjust from the full rate AMR mode to the half rate AMR mode so that the AMR source encoding rate of information sent to first node does not exceed the half rate data transmission rate over the radio interface.

Information may be sent to the second node so that the second node changes from the current AMR source bit rate to the new AMR source bit rate in multiple steps. In the GSM example application, multiple codec mode request or commands may be sent to the second node to stepwise adjust from the full rate AMR mode down to the half rate AMR mode The commanding step may include a handover command to cause the first node to start transmitting at the second data transmission rate over a half rate radio channel. After the handover is performed, the second node's AMR encoder generates source data based on the new AMR source bit rate. By the time the handover is performed, the second node's AMR encoder is generating source data based on the new AMR source bit rate. The handover is orchestrated by a base station controller that controls one or more base stations involved in the handover.

In the non-limiting GSM example application, the handover may be orchestrated by a base station system that controls two or more base stations controllers that each control one or more base stations involved in the handover.

Another aspect of the technology includes determining a round trip time associated with the communication between the first node and second node, where the predetermined delay period is based on the round trip time.

DETAILED DESCRIPTION

In the following description, for purposes of explanation and non-limitation, specific details are set forth, such as particular nodes, functional entities, techniques, protocols, standards, etc. in order to provide an understanding of the described technology. In other instances, detailed descriptions of well-known methods, devices, techniques, etc. are omitted so as not to obscure the description with unnecessary detail. Individual function blocks are shown in the figures. Those skilled in the art will appreciate that the functions of those blocks may be implemented using individual hardware circuits, using software programs and data in conjunction with a suitably programmed microprocessor or general purpose computer, using applications specific integrated circuitry (ASIC), programmable logic arrays, and/or using one or more digital signal processors (DSPs).

The following non-limiting examples are provided in the context of a GSM based communications system. However, those skilled in the art will appreciate that the technology described here may be used in any digital network using radio and/or wired connections and using some kind of coding of digital voice or speech information.

Adapting the coding rate of source information is called codec mode adaptation and allows adapting the degree of error protection. At a given, fixed bit rate, the amount of bits used for transmitting the source information and the amount of redundancy bits that are added for protecting the channel from faulty transmitted bits may be bit varied. A speech codec built according to the AMR specification includes a number of codec modes with different selectable source bit rates such as: 4.75, 5.15, 5.9, 6.7, 7.4, 7.95, 10.2, and 12.2 kbps. The amount of speech coding in relation to the amount of channel coding can be adapted according the requirements set by current channel conditions. Present channel conditions are determined and used to select a codec mode that provides optimal quality for the detected conditions. Examples of information that may be used to adapt the codec mode includes either channel measurement data indicating the estimated channel quality or capacity or a codec mode request (CMR) informing the sending side about the codec mode that the sending side should select. It should also be understood that in GSM-type systems, there are two radio channel "modes" (not to be confused with AMR codec modes) including a full rate (FR) radio channel and a half rate (HR) radio channel having radio bit rates of 22.8 and 11.4 kbps, respectively. For the GSM example, sixteen preferred configurations of AMR codec mode are defined [see 3GPP 28.062], each including up to four codec modes.

Figure 1:
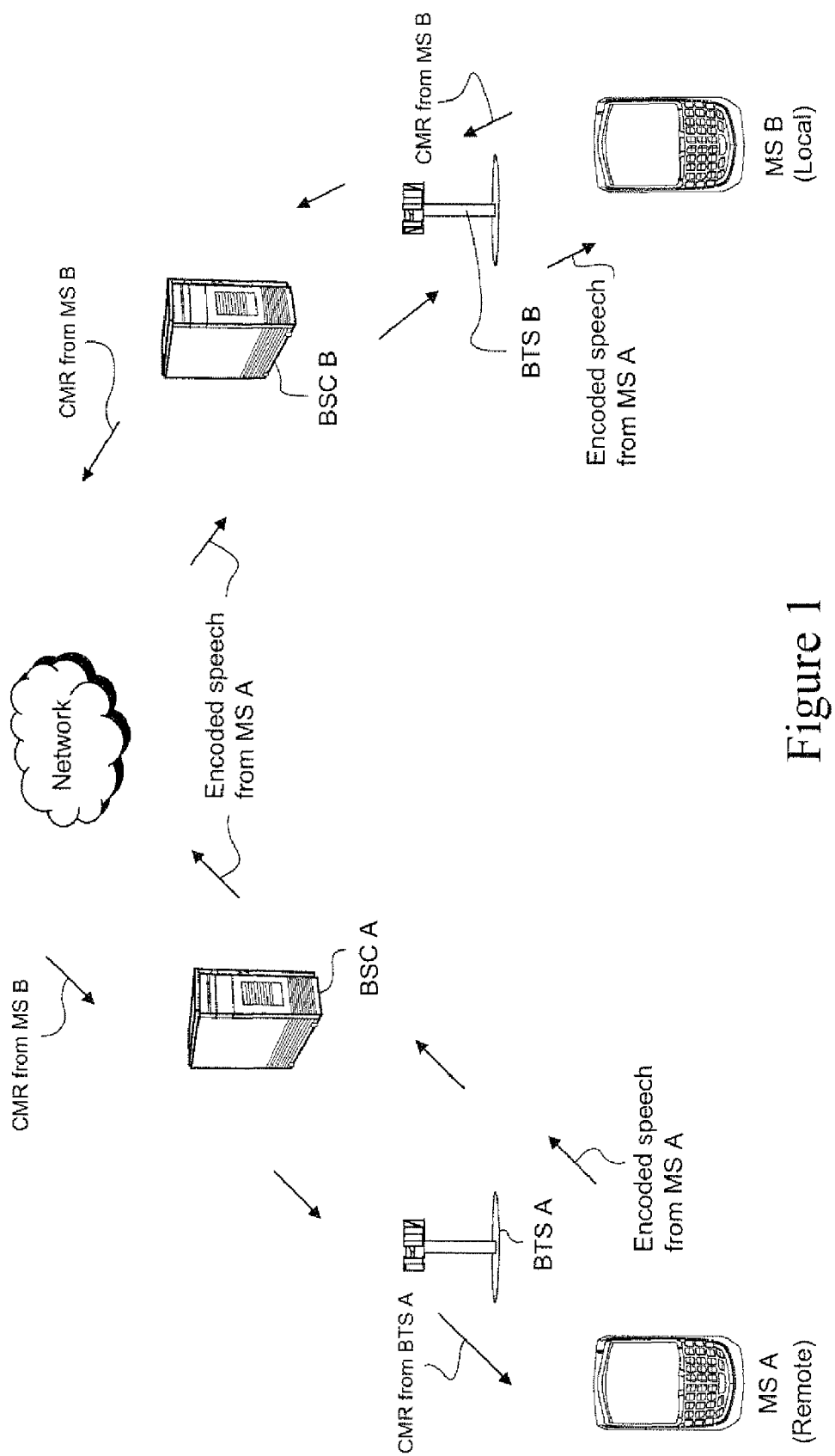
FIG. 1 is a diagram illustrating an example communication between a remote host mobile radio MS-A and a local host mobile radio MS-B.

Reference is now made to an example wireless communication shown in FIG. 1 which is in the non-limiting context of a GSM type system. A mobile station MS-A, corresponding to a remote host, has established a communication with a mobile station MS-B, corresponding to a local host. Both mobile stations A and B are transmitting over a radio interface using a full rate (FR) radio channel. In addition, both mobile stations A and B have AMR encoders which have been selected to operate in the 12.2 kbps AMR mode consistent with a full rate (FR) radio channel. Accordingly, encoded speech from mobile MS-A is transferred via base station BTS-A, base station controller BSC-A, one or more networks, such as a core network, the internet, etc., BSC-B, BTS-B, and then across the radio interface to the local mobile host MS-B. The local mobile host MS-B detects the channel quality of the information received over the radio interface from BTS-B, and based thereon, transmits a corresponding, suitable CMR back to the remote host MS-A in the reverse path.

Figure 2:
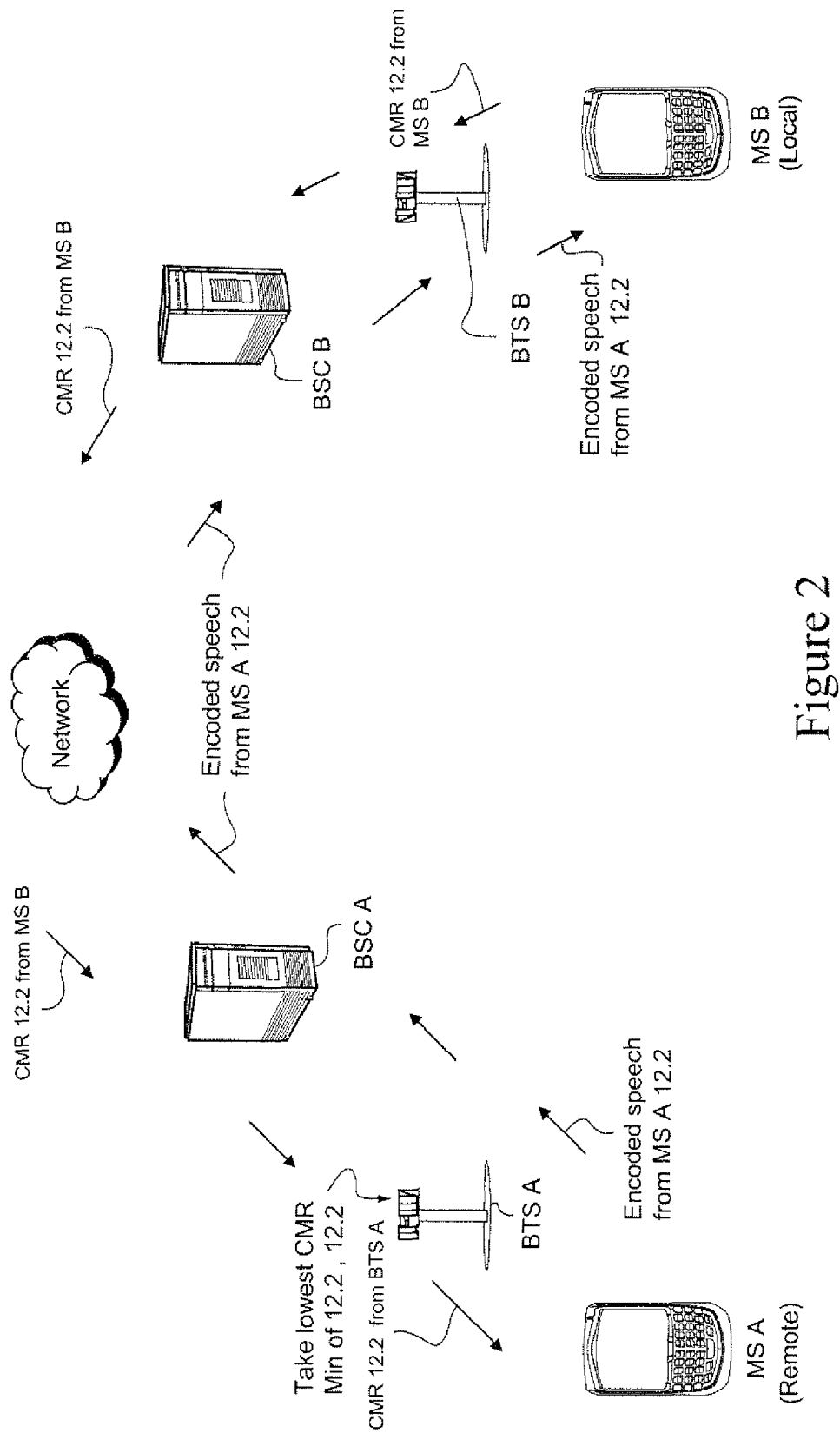
FIG. 2 takes the example communication from FIG. 1 and provides initial AMR encoding rates assuming full rate radio channels for both the remote and local host mobile stations.

FIG. 2 shows the example in FIG. 1 in which the full rate radio channels and AMR codec mode 12.2 are labeled.

Figure 3:
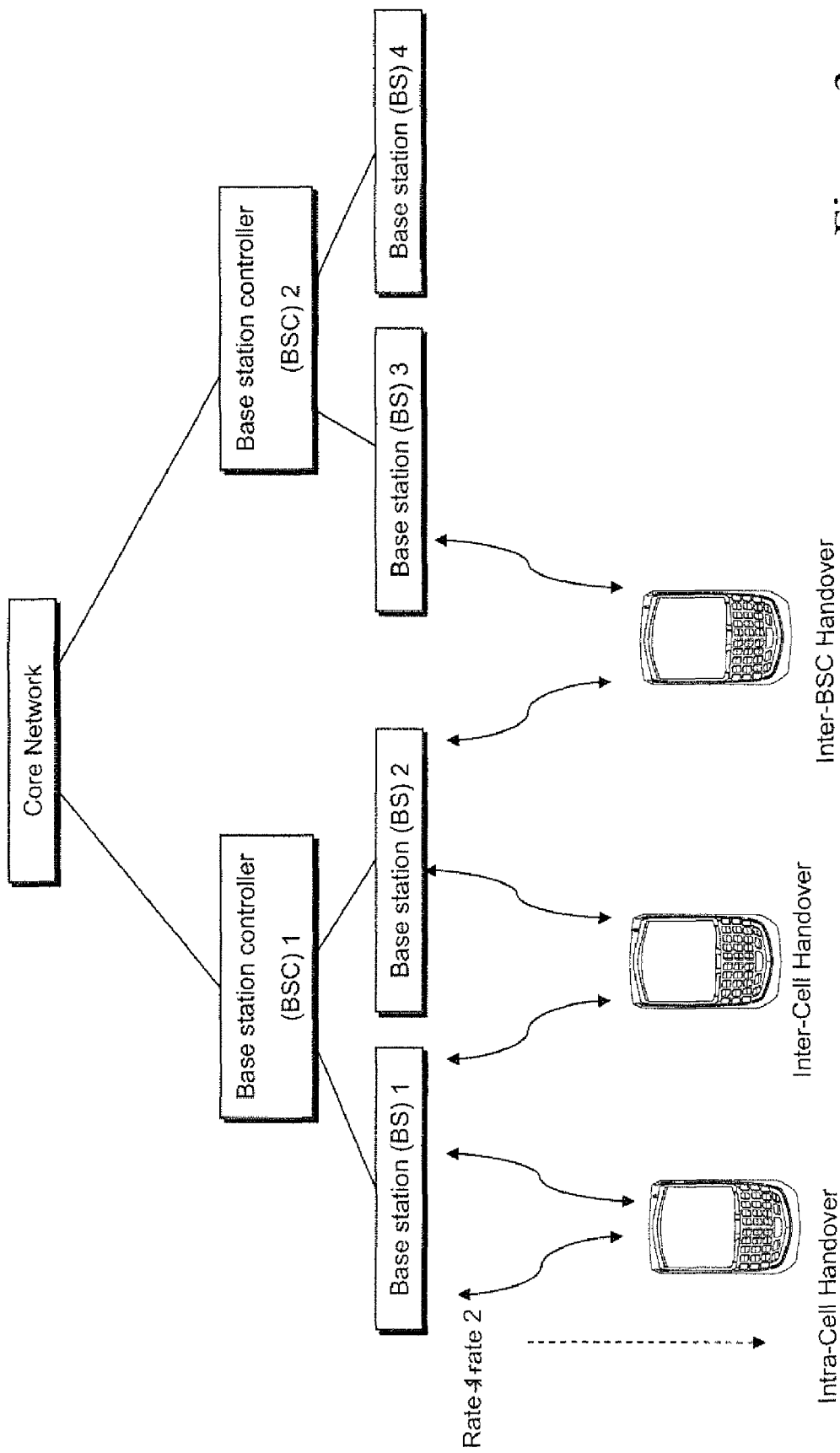
FIG. 3 is a non-limiting, example function block diagram of a GSM based communications system showing a change in data transmission rate over a radio interface for and potential handovers of a mobile station communication.

There are situations in which it is necessary to change the radio channel transmission rate and/or the radio channel for one or more of the mobile stations A and B during the communication. FIG. 3 is a non-limiting, example function block diagram that helps illustrate these potential changes in a GSM type system. A call is controlled by a mobile switching center (MSC) node in the core network, and this node is coupled to and supervises two (or more) base station controllers (BSCs) BSC1 and BSC2. BSC1 supervises two (or more) base stations BS1 and BS2 and base station controller BSC2 supervises two (or more) base stations BS3 and BS4. The mobile station communicates over the radio interface at a data transmission rate 1 with base station. BS1. A condition is detected that makes it necessary to change that transmission rate to a second radio channel transmission rate 2 while still connected to BS1 (i.e., an intra-BSC, inter cell handover). Alternatively, the mobile station may be moving so that it no longer is in range of base station BS1 but instead moves into range with BS2 (i.e., an intra-BSC, inter cell handover). In this case, a handover is performed changing the radio channel over which the mobile station is transmitting. Still further, if the mobile station continues to move out of range from base station 2 toward base station BS3, an inter-BSC handover is performed from BS2 to BS3. Each of these situations may impact the AMR coding rate in the example of FIG. 2 to be used by the local and remote host mobile stations in their communication.

Figure 4:
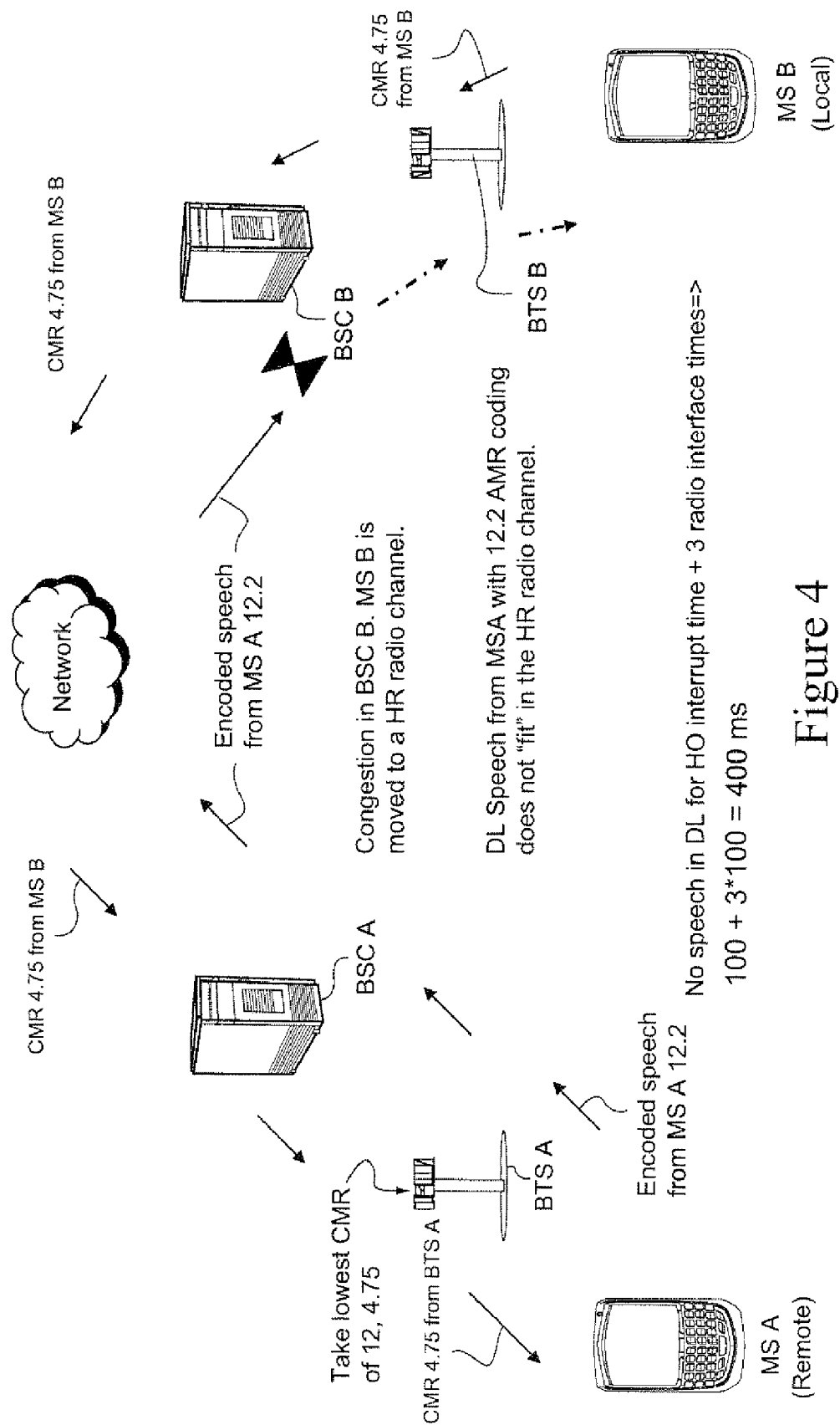
FIG. 4 continues with the example from FIG. 2 showing a problem situation when a radio channel transmission rate for MSB decreases.

Such impact is illustrated in a problem situation shown in FIG. 4 using the same example from FIG. 2. At some point in time during the communication between MS-A and MS-B, BSC-B detects congestion either in the cell being serviced by BTS-B in which local host MS-B is transmitting or in a cell in BSC-B to which MS-B must be moved due to radio coverage in the radio network where BSC-B is located. Other congestion conditions may also be detected such as overload in transmission network between BSC-B and BTS-B. Base station controller B then sends a command via BTS-B to move the mobile MS-B from a full rate radio channel to a half rate radio channel. In addition, BSC-B also indicates to MS-B that when starting to use the new radio channel the AMR mode for the codec in the mobile station (MS-B) should be decreased to an AMR mode that is consistent with a half-rate radio channel. In this example, an AMR mode of 4.75 kbps is selected. As a result, MS-B sends a. CMR message of 4.75 in the reverse path towards remote host MS-A.

Unfortunately, there is a significant delay before MS-A receives that new CMR of 4.75 kbps. In the meantime, MS-A continues to send encoded speech at a 12.2 kbps AMR mode, and when it reaches BTS-B, does not "fit" into the new half rate radio channel to MS-B. As a result, the speech frames that do not fit are discarded by BTS-B, resulting in audible distortion detectable to the user of MS-B. As indicated in the bottom of FIG. 4, an example of a delay before MS-A decreases its AMR coding rate may be on the order of 400 milliseconds, meaning that 400 milliseconds of speech might need to be discarded by BTS-B.

Figure 5A:
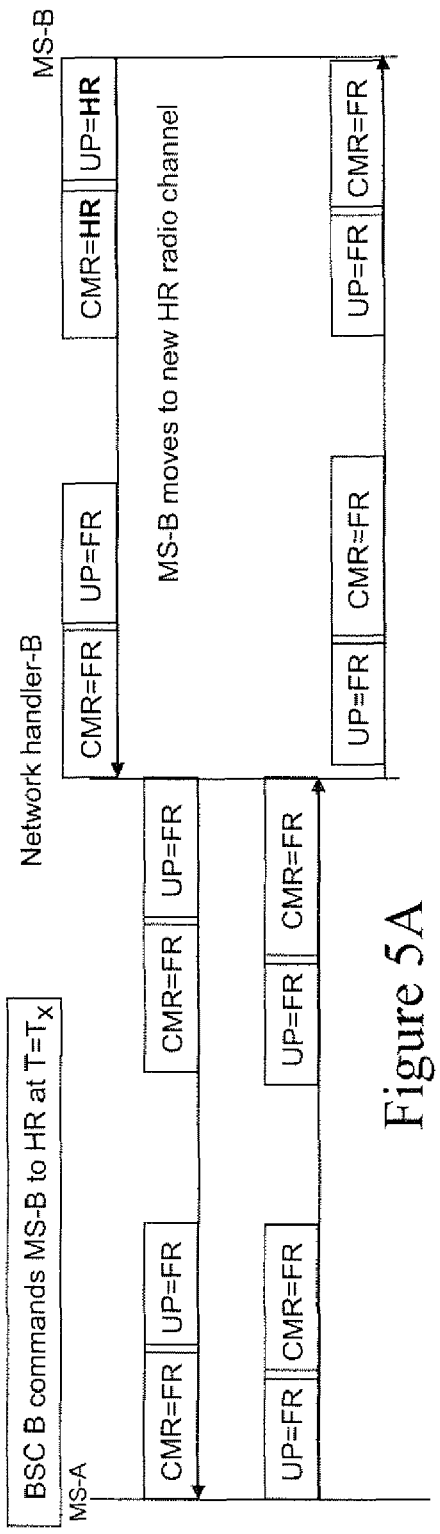
FIGS. 5A-5C are timelines that illustrate the various messages and information sent in the example of FIG. 4.
Figure 5B:
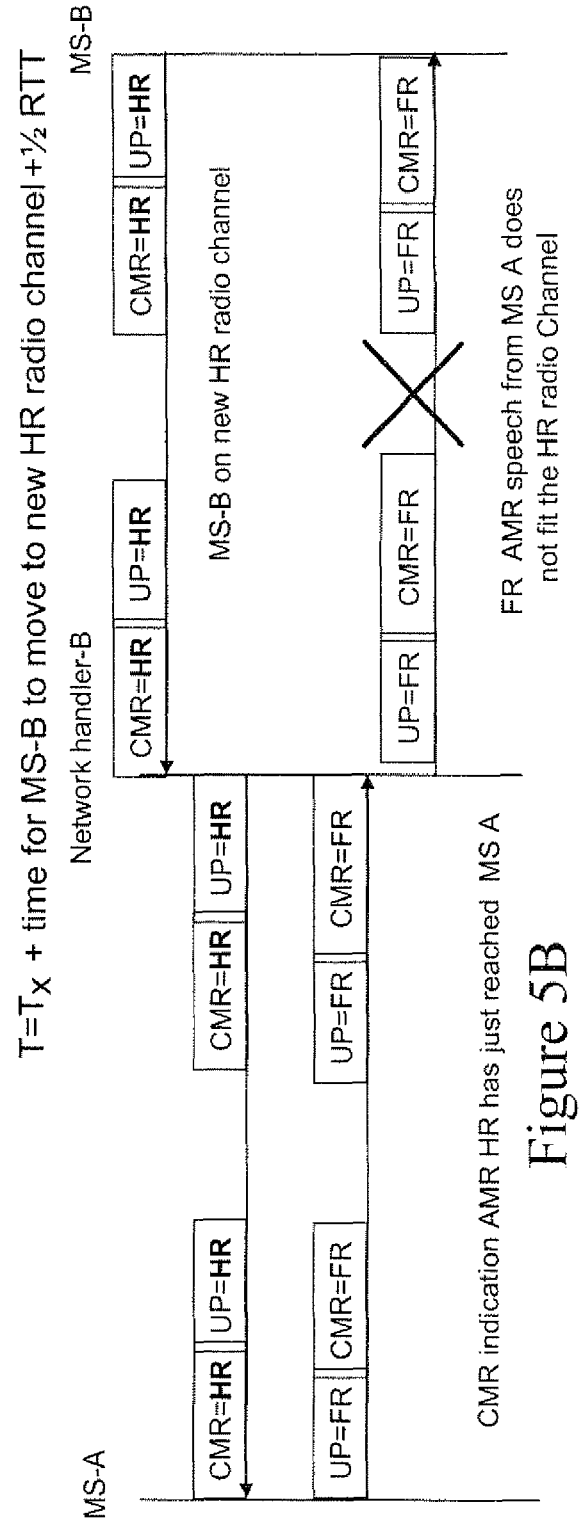
Figure 5C:
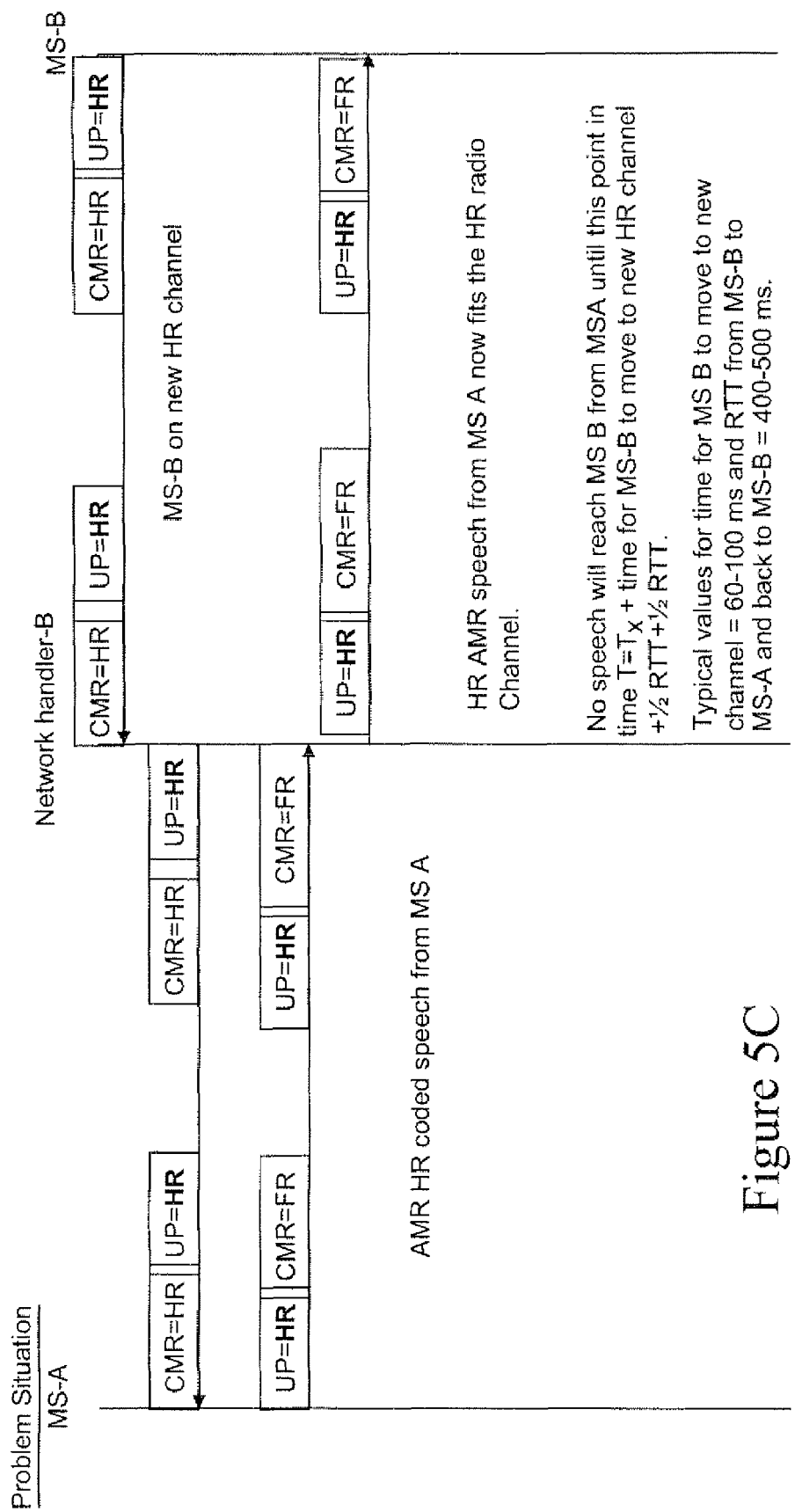

FIGS. 5A-5C are timelines that illustrate the problem situation identified in the example of FIG. 4. In FIG. 5A, BSC-B commands MS-B to move to a half rate radio channel at time equals $T_x$. At that point, MS-B changes its transmission in the uplink (UP) to half rate (HR) and also sends a CMR equal to a half rate AMR mode of 4.75 kbps.

In FIG. 5B, the elapsed time increases to $T_x$ plus the time for MSB to move to a new, half rate radio channel plus half of the roundtrip time (RTT) needed for the new half rate (FIR) CMR message to reach MS-A. Unfortunately, uplink speech frames from MS-A continue to arrive at full AMR rate, and thus, cannot fit into the half rate radio channel to MS-B.

FIG. 5C illustrates a situation where sufficient time has transpired such that mobile station A has now switched to transmitting at a half rate AMR mode and those half rate AMR mode speech frames are now being received by MS-B. As noted at the bottom of FIG. 5C, speech from MS-A to MS-B is interrupted for time $T=T_x$ plus the time for MSB to move to a new half rate channel plus the full RTT from MS-B to MS-A and back to MS-B. Typical example values for this time T are on the order of 400 to 500 milliseconds.

The following technique avoids this interrupted speech problem that is both effective and easy to implement. Using the non-limiting example from FIG. 4, a new AMR source coding mode request is sent to MS-A before the radio channel transmission rate for MS-B changes. After a sufficient time transpires so that MS-A can change its AMR source coding mode/bit rate to a new AMR source coding mode/bit rate consistent with the radio channel transmission rate change for MS-B, or after MS-A indicates in any appropriate fashion that it has changed to the new AMR source coding mode/bit rate, the change to the second data transmission rate over the radio channel to MS-B is made.

Figure 6:
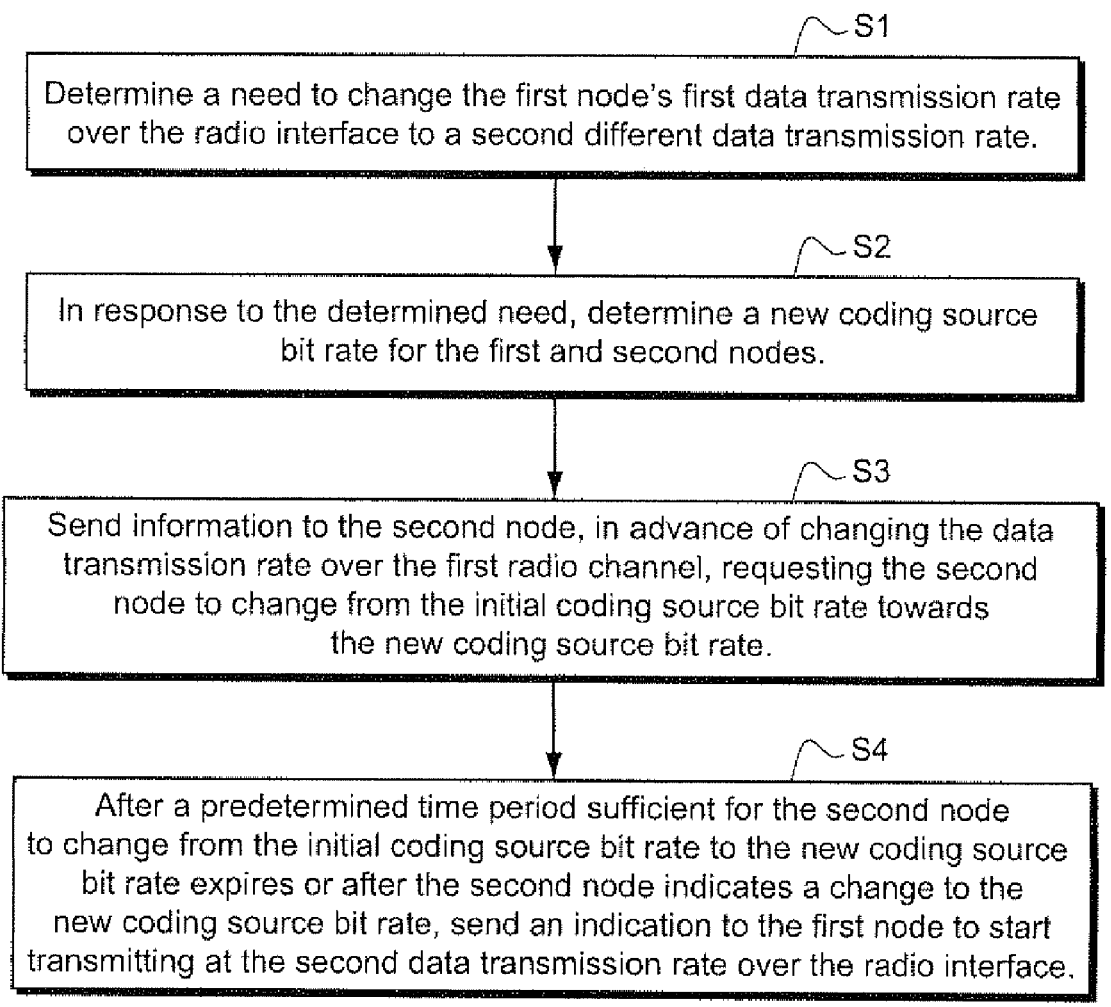
FIG. 6 is a flowchart diagram illustrating non-limiting example procedures for solving the problem illustrated in FIG. 4 and FIGS. 5A-C.

A non-limiting example of more general procedures that may be followed for implementing the solution to the problems identified above is now described in conjunction with the flow chart in FIG. 6. These procedures may be implemented in a control node in or associated with the radio network. In the GSM example, such a control node might be a BSC, BTS, or BSS. FIG. 6 assumes a communication is established between a first node and a second node. In step S1, a need is detected for changing the first node's transmission rate over the radio interface to a second different transmission rate. In response to that determined need for change, a new coding source bit rate is determined for both the first and second nodes (step S2). Information is then sent to the second node in advance of changing the transmission rate over the radio interface requesting the second node to change from the initial coding source bit rate towards the new coding source bit rate (step S3). After a predetermined time period (sufficient for the second node to change from the initial coding source bit rate to the new coding source bit rate) expires or after the second node indicates a change to the new coding source bit rate, an indication is sent to the first node to start transmitting at the second data transmission rate over the radio interface (step S4). Advantageously, no adverse impact on speech quality is experienced by a first node user, and radio transmission resources are conserved that would otherwise be wasted trying to transmit speech frames over the radio interface that do not "fit."

In-band signaling is preferably used to send the information in step S3 to avoid having to send separate control signaling out of band. But out of band control signaling may be used.

Figure 7:
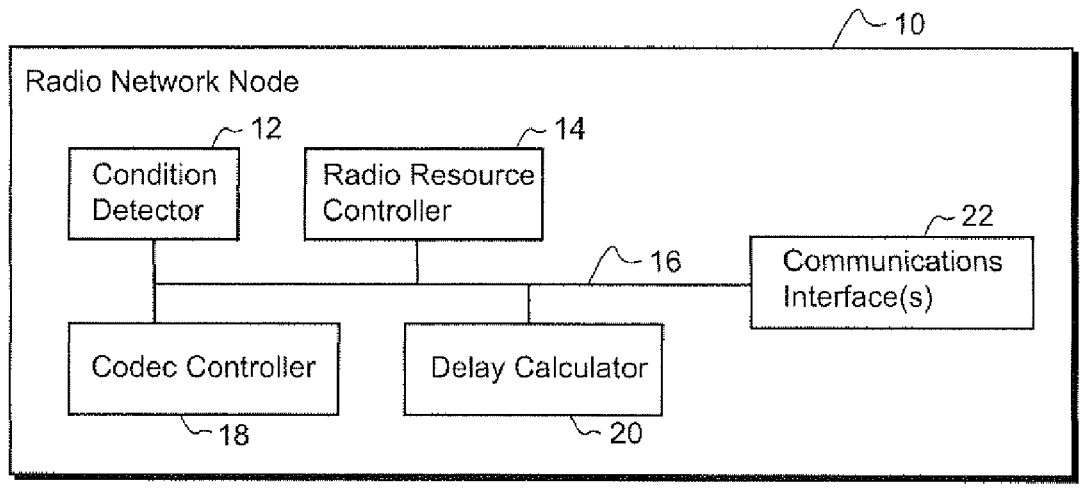
FIG. 7 is a non-limiting example function block diagram of a radio network node that may be used to implement the procedures of FIG. 6.

FIG. 7 illustrates a non-limiting function block diagram of a general radio network node 10 that may be used to implement the procedures outlined in the flowchart of FIG. 6. The radio network node includes a condition detector 12 for determining a condition that indicates a need to change the data transmission rate over the radio interface or a radio channel for a mobile station, (referred to for convenience as the local mobile station), involved in a radio communication being supervised by that radio network node 10. The condition detector 12 provides that detected condition over a bus 16 to a radio resource controller 14 which makes a decision based on the detected condition to change the data transmission rate over the radio interface for the local mobile station or to handover the local mobile station to a new radio channel with a different data transmission rate. This decision by the radio resource controller 14 is coordinated with a delay calculator 20 which determines a predetermined delay period before the radio resource controller sends the command for changing the data transmission rate used by the local mobile station via a communication interface 22. The radio network node 10 may also have other communication interfaces to other nodes. The delay calculator 20 may take into account such factors as roundtrip time (RTT) between the local and remote host nodes, times for the local mobile station node to move to a new channel, processing times in each node, etc. Any suitable procedure for determining an estimate of the RTT may be used. The radio resource controller 14 also communicates with codec controller 18 which generates commands or requests for changing the AMR codec mode or rate at the local and remote host nodes.

Waiting for the predetermined delay period before sending the command for changing the transmission rate used by the local mobile host node allows sufficient time for the remote host node to adjust its AMR source encoding rate to the new AMR source encoding rate so that the AMR source encoding rate of information sent to local host mobile node is compatible with the new transmission rate over the radio interface.

Figure 8:
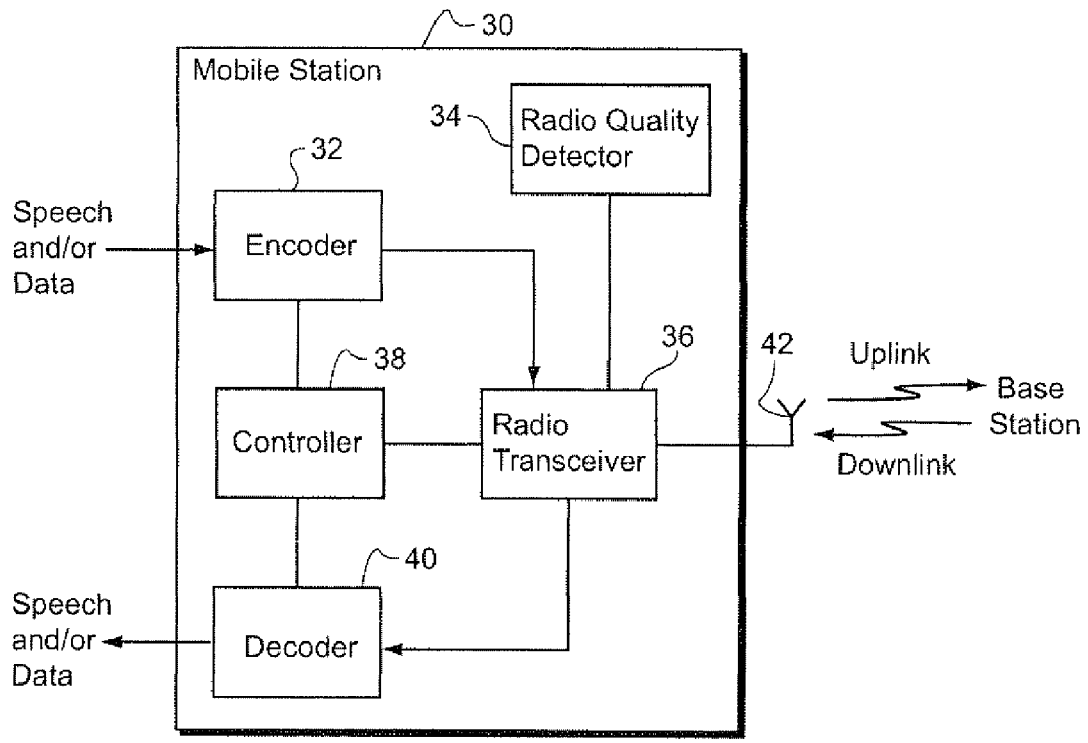
FIG. 8 is a non-limiting example function block diagram of a mobile station.
Figure 9:
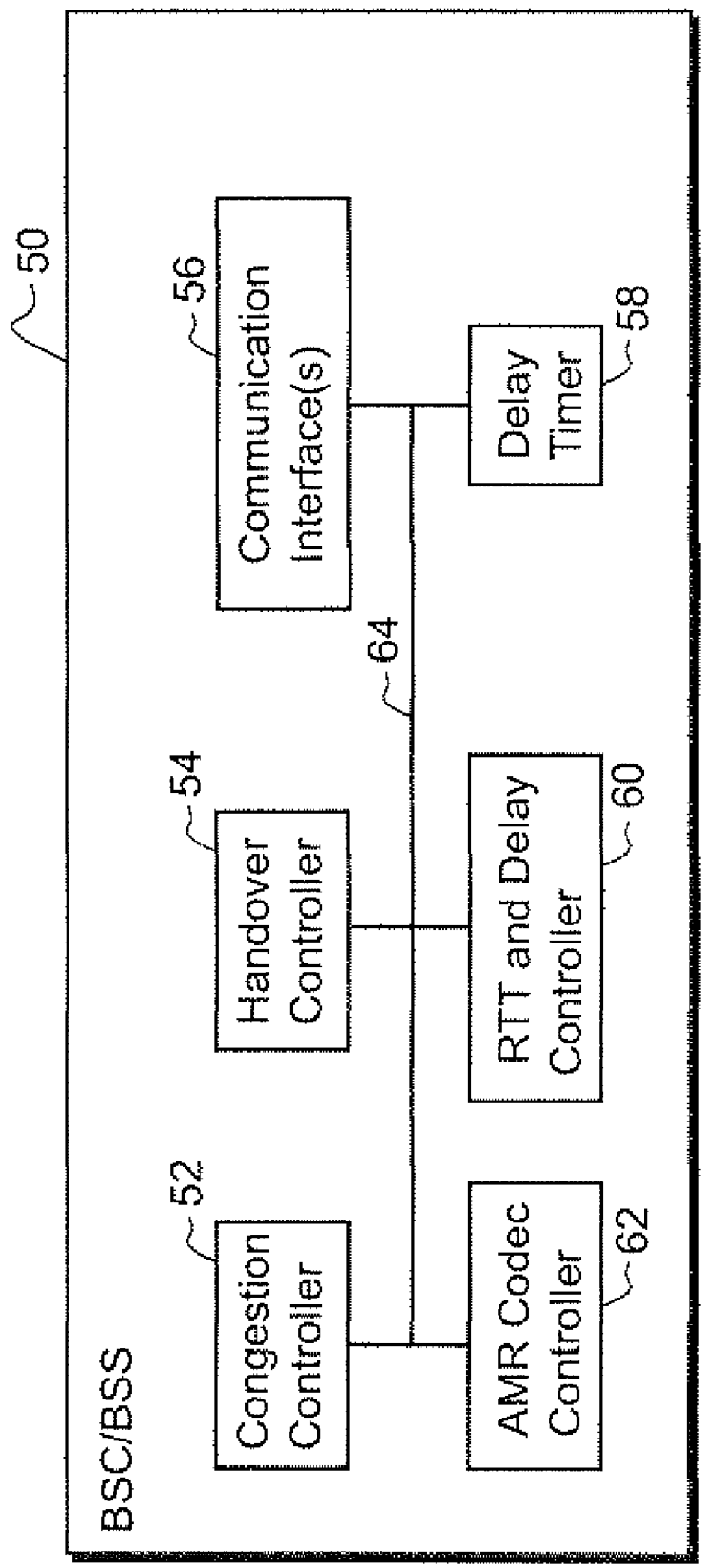
FIG. 9 is a non-limiting example function block diagram of a BSC node or BSS node that may be used to implement the procedures outlined in FIG. 6 in a GSM-based communications system.

FIG. 8 is a non-limiting, example function block diagram for a mobile station 30. The mobile station 30 includes a speech/channel encoder 32 that can adopt different modes of coding or different coding schemes having different degrees of robustness. A radio quality detector 34 senses and/or analyzes the condition of the downlink radio channel and provides a quality indication, e.g., a CMR signal, via radio transceiver 36 on the uplink to the base station. Downlink information from the base station is received via the radio transceiver and provided to a speech/channel decoder 40. The decoder 40 decodes the received signal to produce speech signals that are made audible to the user of the mobile station. Furthermore, the decoder 40 also decodes or detects in the received signal codec information derived from and/or indicating/including the measured quality or condition of the uplink channel. This information can be or include a codec mode request or command is provided to the encoder 32 via the controller 28 to set the encoder 32 to operate in the codec mode corresponding to the request/command.

A non-limiting example of a more specific radio network node in a non-limiting example GSM-type system is now described in conjunction with the non-limiting function block diagram of a BSC or BSS node 50. Node 50 includes a congestion controller 52, handover controller 54, communication interface(s) 56, delay timer 58, RTT and delay controller 60, and AMR codec controller 62 coupled together via bus 64. The congestion controller 52 detects a congestion situation that might warrant a change of radio channel transmission rate or handover for one of the mobile stations in a communication being handled by a base station ultimately being supervised by node 50. The handover controller 54 determines whether or not a change in radio channel either to one having a different transmission rate or to a different channel altogether is necessary. If a change is determined to be necessary, the handover controller 54 informs the RTT and delay controller 60 and the AMR codec controller 62. New AMR source bit rate/mode CMRs are provided for delivery to both the mobile stations A and B, preferably using in-band signaling. The RTT and delay controller 60 determines the predetermined delay time and inputs it to the delay timer 58. When the timer 58 expires, the handover controller 54 sends a command or other signal indicating that the radio transmission rate/channel change should be implemented.

Figure 10:
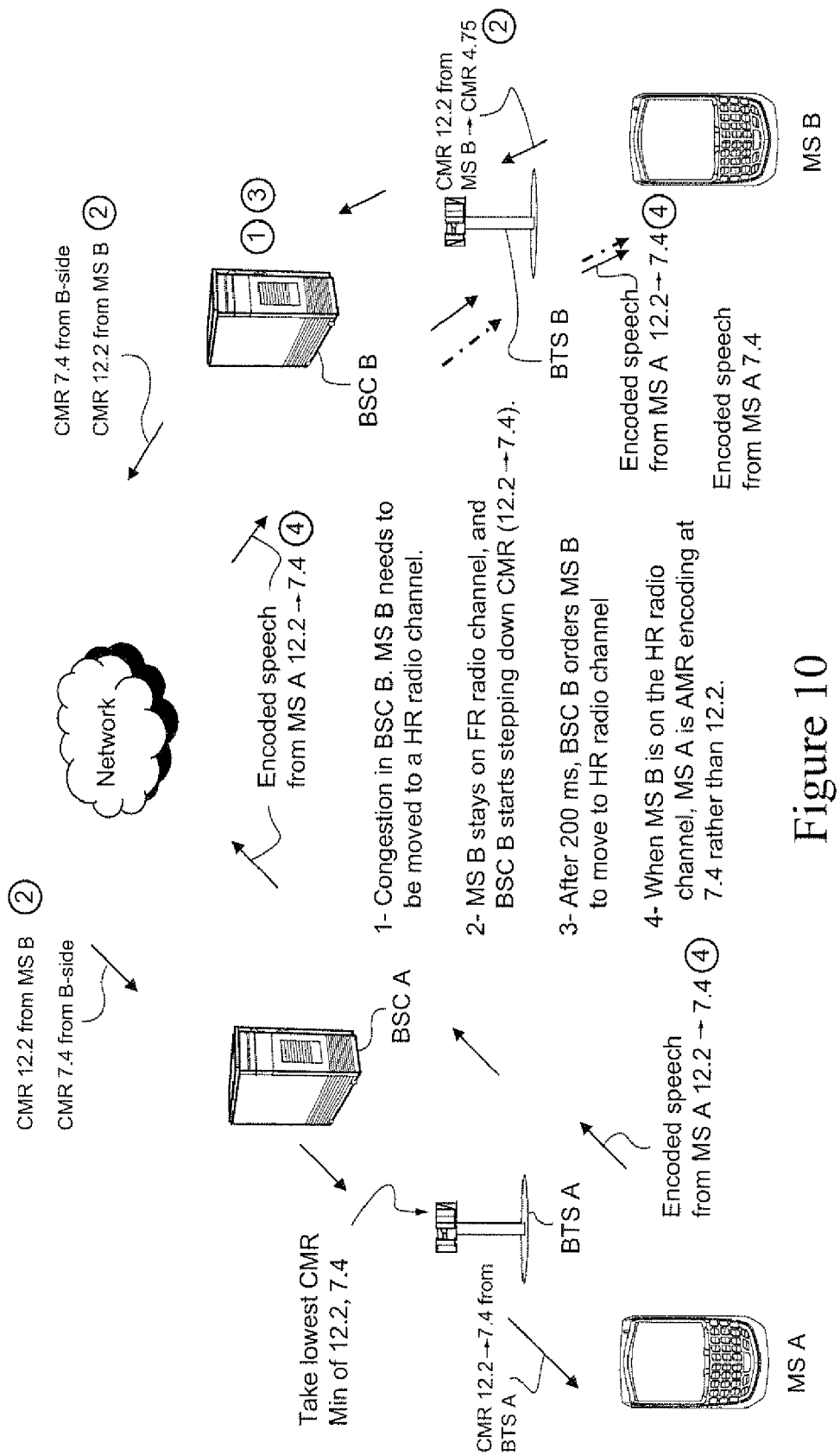
FIG. 10 continues with the example from in FIGS. 1, 2, and 4 but with the problem situation solved using the approach outlined in FIG. 6.

Reference is now made to the example shown in FIG. 10 in which the above described technology is applied to solve the problems noted in FIG. 4 and FIGS. 5A-5C. As in FIG. 4, the initial communication between mobiles MS-A and MS-B is based on a GSM full rate (FR) radio communications channel between mobile MS-B and its base station BTS and between mobile MS-A and its base station BTS-A as well as both mobiles A and B generating encoded speech at the full rate AMR mode 122 kbps. As indicated at point 1, congestion is detected by BSC-B sufficient to require that mobile MS-B be moved to a half rate radio channel. But the shift to a half rate radio channel does not yet occur. Instead, MS-B continues to use the full rate radio channel.

The BSC-B then starts stepping the down the CMR sent from the B side from 12.2 first to 7.4 kbps then further to 5.90 kbps, preferably using in-band signaling. After approximately 200 milliseconds, which corresponds to a non-limiting example predetermined delay time, the BTS-B orders MS-B to move to a half rate radio channel. After receiving that order, MS-B moves to a half rate radio channel and starts transmitting at the half transmission rate at a time when the mobile MS-A is now AMR encoding at 7.4 kbps or lower rather than at 12.2 kbps. As a result, the AMR encoded speech from MS-A at 7.4 kbps (or lower) can "fit" in the half rate radio channel between base station BTS-B mobile station MS-B. In this way, no speech frames are lost, and there is no distortion of the speech from MS-A to MS-B as there was in the situation shown in FIG. 4. The adverse impact on speech quality experienced by the user of MS-B in FIG. 4 is advantageously eliminated.

Figure 11A:
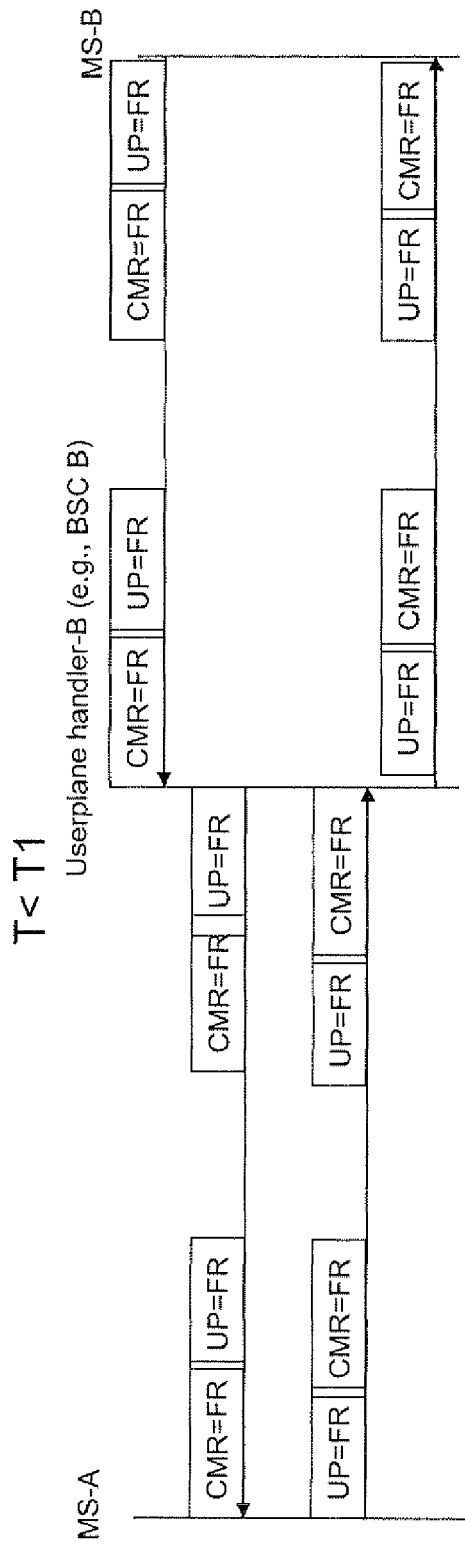
FIGS. 11A-11F are timelines to help explain the progression of signaling and status of the example in FIG. 10 at various times.
Figure 11B:
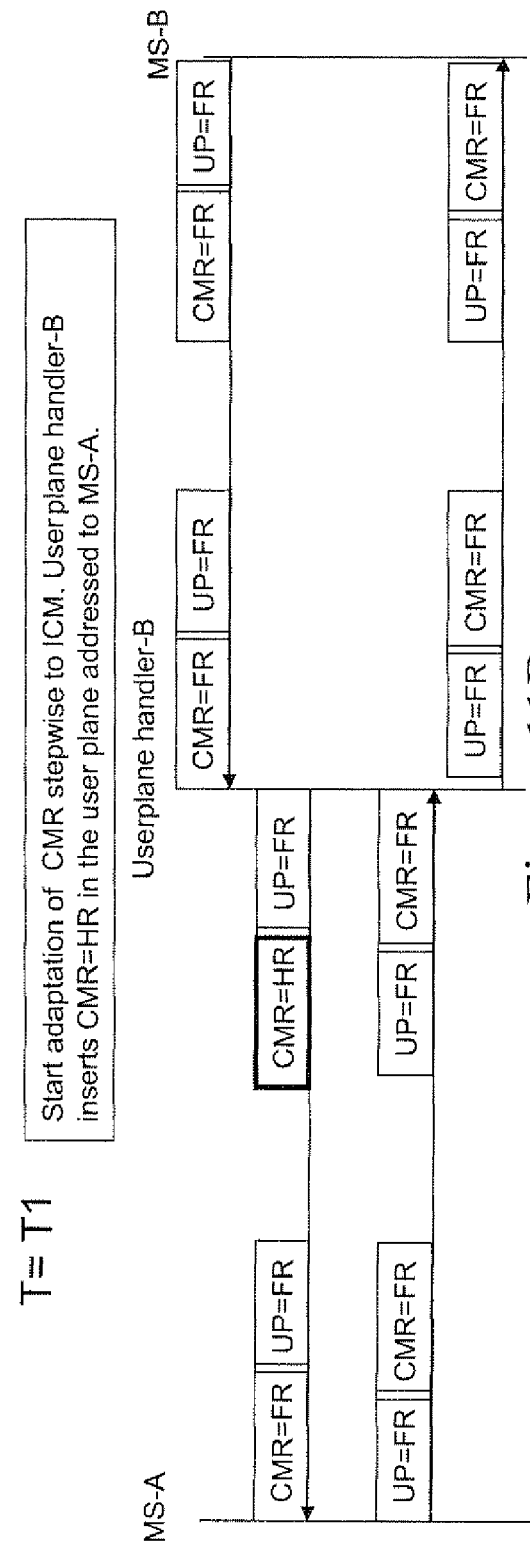

Reference is now made to the timelines in FIGS. 11A-11F which highlight the advantage of the technique just described for FIG. 10 as compared to the timelines FIG. 5A-5C described above. FIG. 11A shows the situation at a time before time T1 and both mobiles MS-A and MS-B are transmitting in the uplink on a full rate (FR) radio channel and are sending CMRs corresponding to a full rate AMR mode. In FIG. 11B, the time has reached T1 where a user plane handler B, e.g., in BSC-B, determines that there is a need to change the radio transmission rate of MSB. The user plane handler B inserts a CMR corresponding to a half rate AMR mode in the user plane speech frames addressed to MS-A. Note that at time T1, there is no change in the uplink full rate channel transmission over the radio channel from the mobile station MS-B.

Figure 11C:
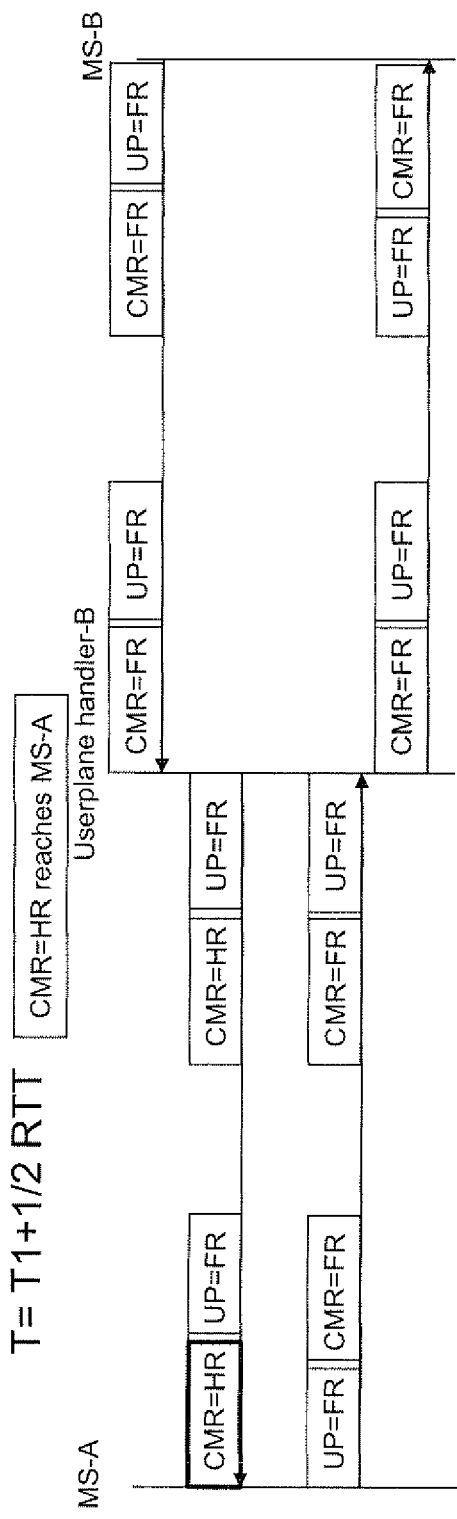
Figure 11D:
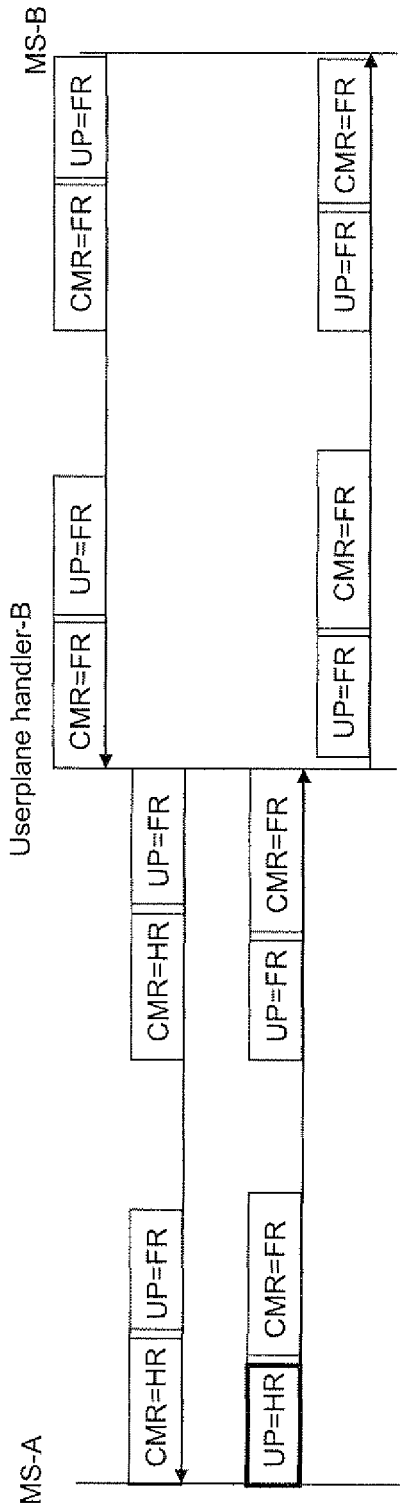

In FIG. 11C, the time has progressed from T1 to T1 plus one half RTT. At this time, the AMR half rate mode CMR message has reached MS-A. Again, MS-B continues to transmit over the radio channel at full rate. FIG. 11D shows time T1 plus one half RTT plus the reaction time at MS-A needed for MS-A to adapt to a half rate AMR mode on the user plane. See the bolded block UP equals HR generated at MS-A.

Figure 11E:
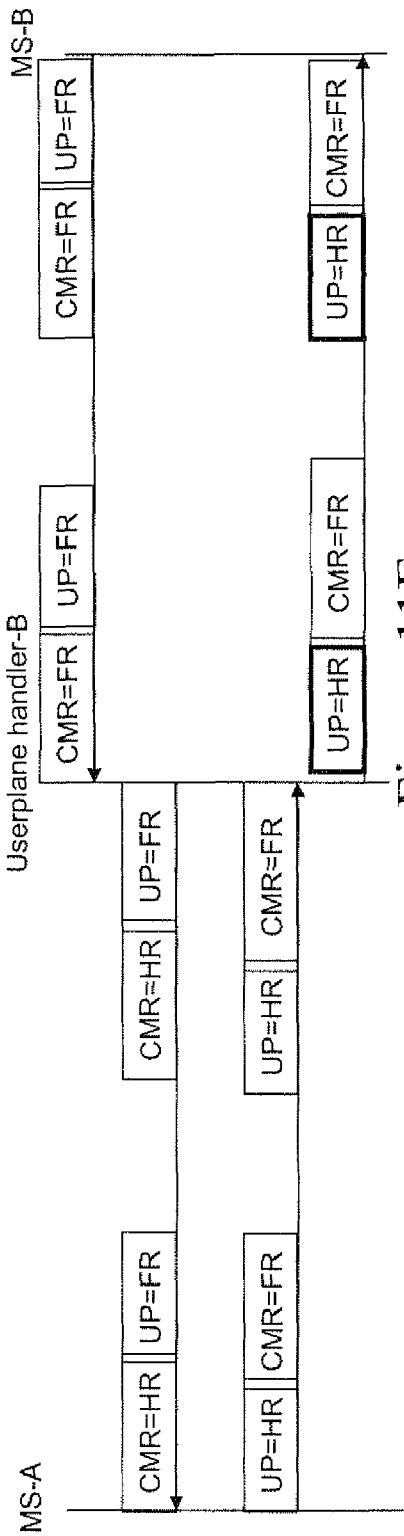
Figure 11F:
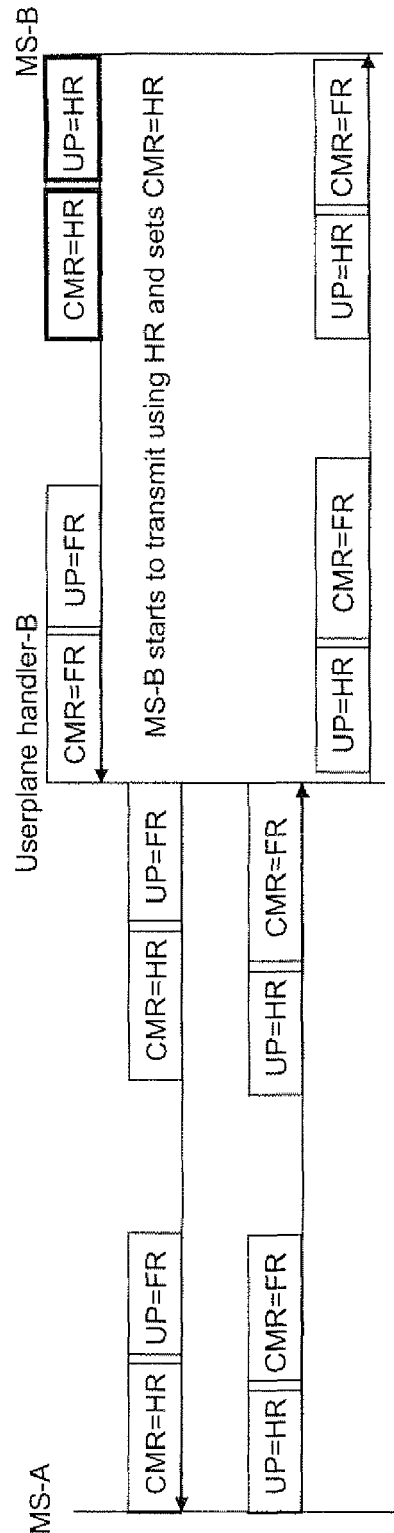

FIG. 11E shows time T1 plus a complete RTT plus a reaction time at MS-B. The AMR half rate information from MS-A has reached MS-B as indicated in the bolded blocks UP equals HR. FIG. 11F shows time T1 plus RTT plus reaction time at MS-B plus a margin of uncertainty time $T_{margin}$. At this point, the BSC commands MS-B to transmit over the radio interface at half rate as indicated in the bolded block UP equals HR. In addition, MS-B also transmits a CMR corresponding to a half rate AMR mode. There is no speech loss or distortion at MS-B as there was in FIG. 5C.

Figure 12:
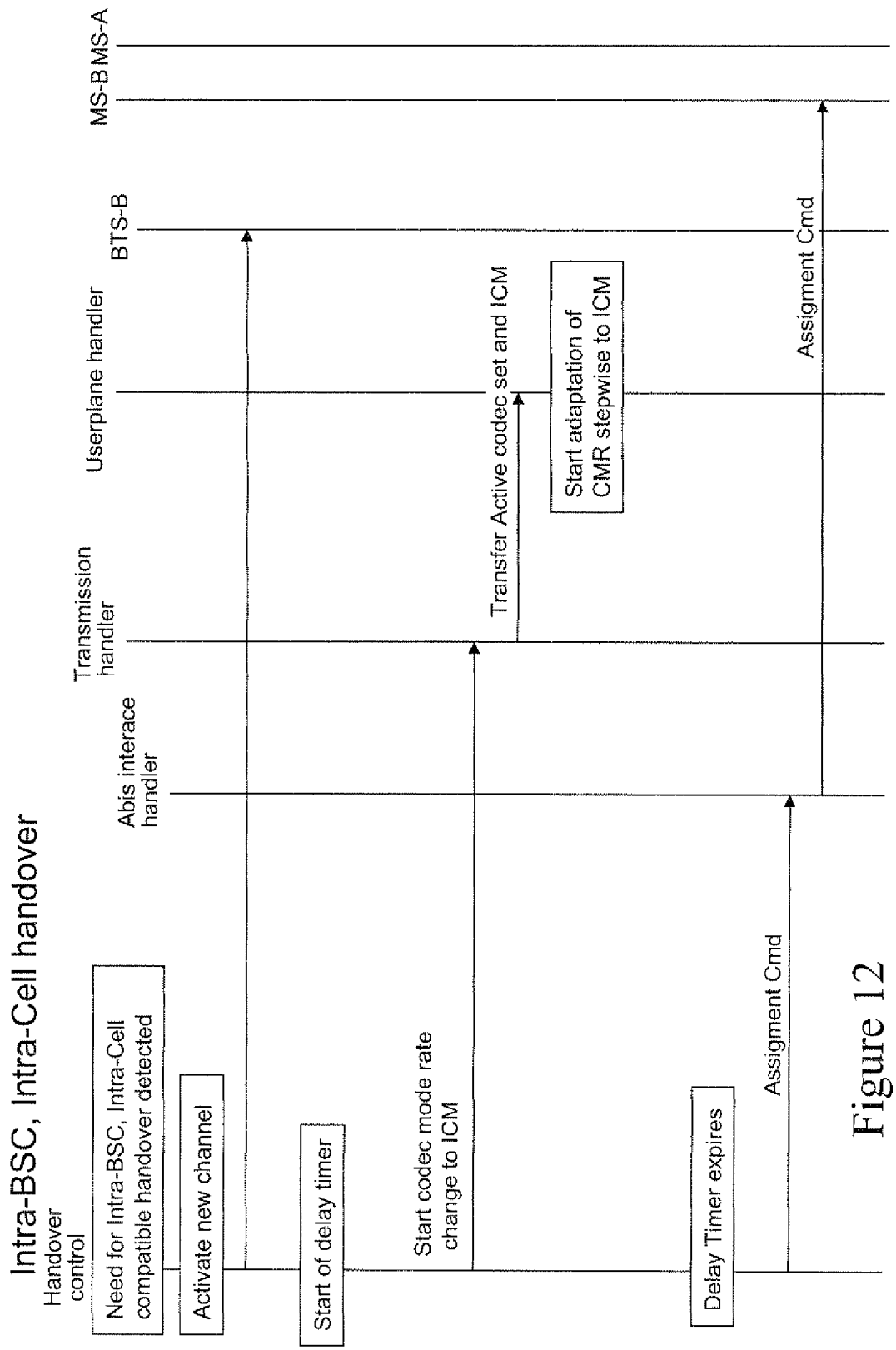
FIG. 12 is a non-limiting example signaling diagram for an intra-BSC intra-cell handover.

FIG. 12 shows an example signaling diagram for an intra BSC intra cell handover implemented in one non-limiting example way in a BSC. Functional entities in the BSC are indicated as vertical lines as labeled at the top of each vertical line with the exception of BTS-B, MS-B, and MS-A. Initially, the handover control and the traffic resources handler are made aware of a need for an intra-BSC, intra-cell compatible handover. The handover controller then provides for a new radio channel for MS-B which is sent to the base station BTS-B. The BTS-B waits however to perform the handover to the new channel. The handover controller also starts the delay timer using the predetermined value calculated as described/shown for example above in FIGS. 11A-11F. The handover control also starts or initiates a codec mode rate change to an initial codec mode (ICM), which in the example above is a switch from AMR codec mode 12.2 to 7.40 and further down via 5.90 to 4.75 kbps, since the CMR is only allowed to step one codec mode every second radio frame. The transmission handler transfers the active codec set and the newly-defined ICM to a user plane handler. The user plane handler then starts (preferably stepwise) adaptation of the CMR that is currently originally sent by MS-B and used by MS-A to the calculated ICM (e.g., from 12.2 stepwise down to 4.75 kbps). After the delay timer expires, the handover control sends a radio assignment command to the Abis interface handler (Abis is the communications interface in the BSC with the BTSs), which then sends a radio assignment change (to the new radio channel) command via BTS-B to the mobile station B. In the example shown in FIG. 10, mobile station MS-B would then switch from full-rate to half rate radio transmission.

Figure 13:
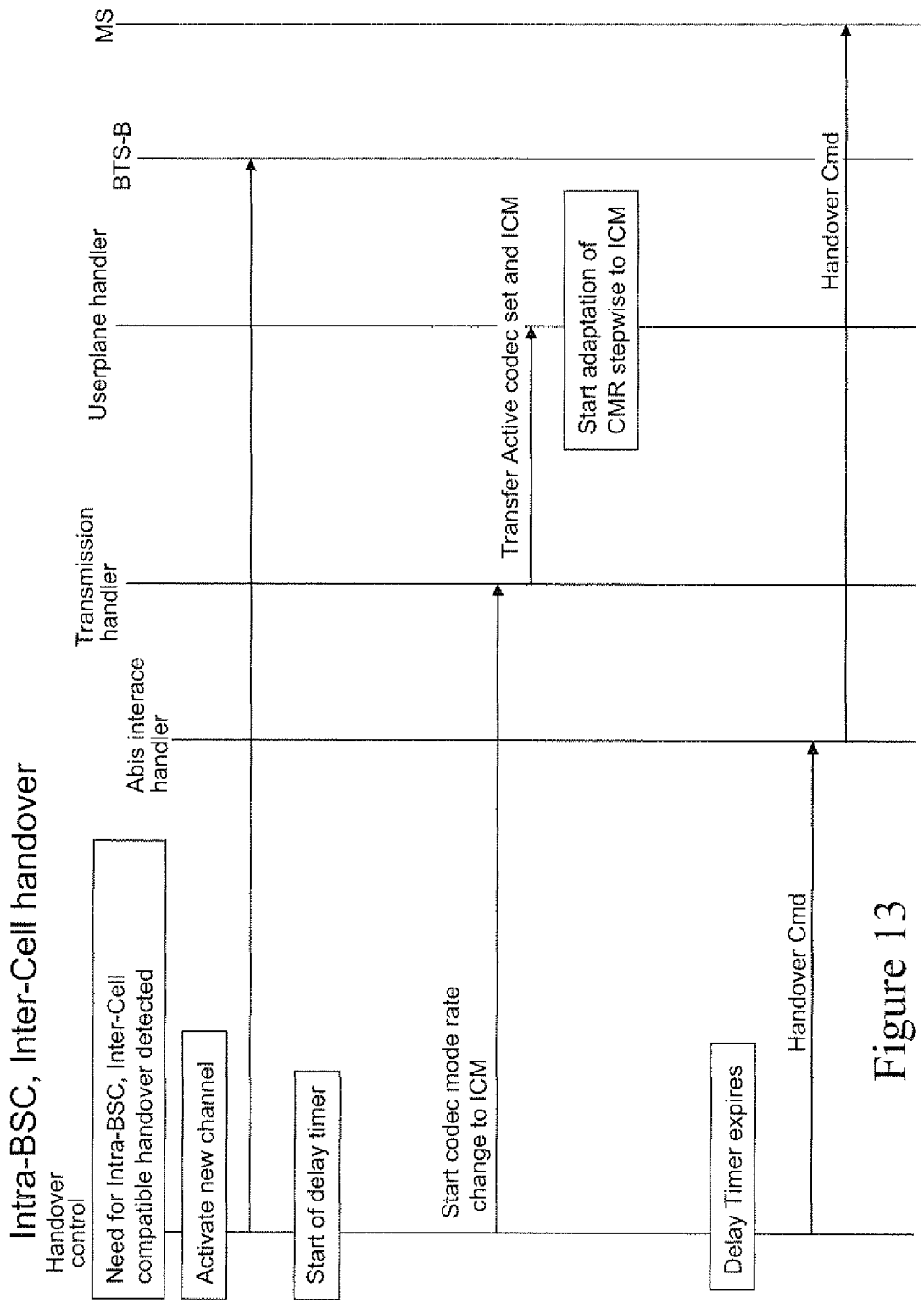
FIG. 13 is a non-limiting example signaling diagram for a variation of the an intra-BSC inter-cell handover shown in FIG. 12.

FIG. 13 is a non-limiting example signaling diagram of an intra-BSC, inter-cell handover similar to that shown in FIG. 12 with the exception that the handover controller in the inter cell case generates a handover command rather than a radio assignment command.

Figure 14:
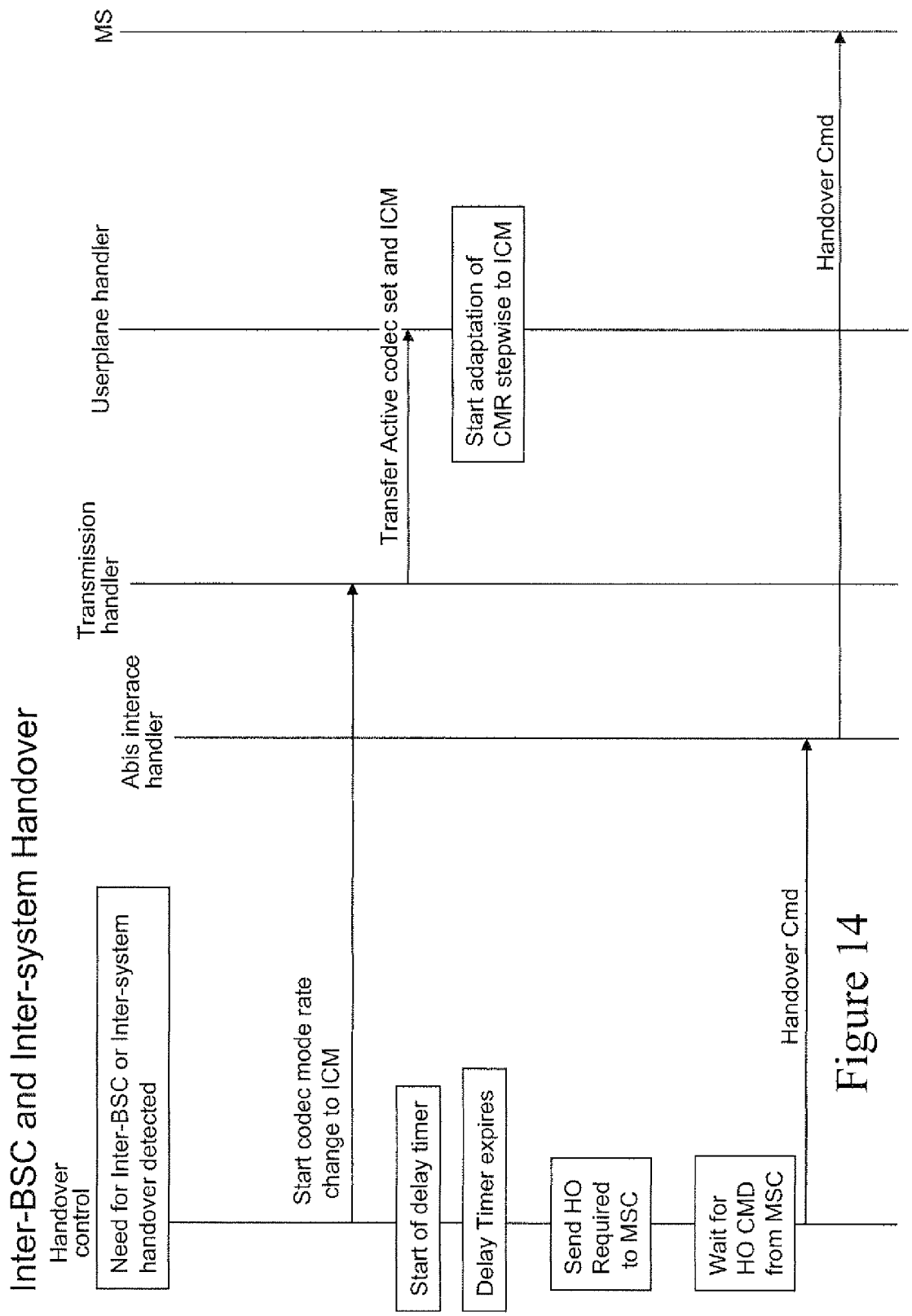
FIG. 14 is a non-limiting example signaling diagram for an inter-BSC or inter-system handover.

FIG. 14 illustrates a non-limiting example signaling diagram for an inter-BSC handover or an inter-system handover. Here the handover is between two base stations that are controlled by two different BSCs or two different systems. Although a delay timer is shown, it may be that extra delay may not be needed due to the time is takes for the MSC—new BSS signaling.

Although various embodiments have been shown and described in detail, the claims are not limited to any particular embodiment or example. None of the above description should be read as implying that any particular element, step, range, or function is essential such that it must be included in the claims scope. The scope of patented subject matter is defined only by the claims. The extent of legal protection is defined by the words recited in the allowed claims and their equivalents. All structural and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. No claim is intended to invoke paragraph 6 of 35 USC §112 unless the words "means for" or "step for" are used. Furthermore, no embodiment, feature, component, or step in this specification is intended to be dedicated to the public regardless of whether the embodiment, feature, component, or step is recited in the claims.

The invention claimed is:

1. A method for controlling Adaptive Multi-Rate (AMR) encoding of speech signals that are to be sent between a first node and a second node in a wireless communication system, where an AMR encoder associated with each of the first node and the second node encodes speech signals in multiple modes having different degrees of robustness that correspond to different AMR source bit rates, where for a communication established between the first node and the second node, the first node transmits over a radio interface at a first data transmission rate, and where the AMR encoders associated with the first node and the second node generate source data for transmission at a first AMR source bit rate, the method comprising the steps of:

determining a need to change the first node's first data transmission rate over the radio interface to a second different data transmission rate;

in response to the determined need, determining a new AMR source bit rate for the first node and the second node;

sending information to the second node, in advance of changing the data transmission rate over the radio interface, requesting the second node to change from a current AMR source bit rate towards the new AMR source bit rate; and after a predetermined time period sufficient for the second node to change from the current AMR source bit rate to the new AMR source bit rate expires or after the second node indicates a change to the new AMR source bit rate, sending an indication to the first node to start transmitting at the second data transmission rate over the radio interface.

2. The method in claim 1, wherein waiting for the predetermined delay period before performing the sending step allows sufficient time for the second node to adjust its AMR source encoding rate to the second AMR source encoding rate so that the AMR source encoding rate of information sent to first node is compatible with the second data transmission rate over the radio interface.

3. The method in claim 1, wherein the information is sent to the second node using in-band signaling in a user plane.

4. The method in claim 1, wherein the information sent to the second node is a codec mode request or command.

5. The method in claim 1, further comprising:
   detecting a condition that indicates a need to change the first node's first data transmission rate over the radio interface.

6. The method in claim 5, wherein the wireless communication system is a GSM-based wireless communication system, the condition is a congestion condition, and the second data transmission rate corresponds to a half rate radio channel and the first data transmission rate corresponds to a full rate radio channel.

7. The method in claim 6, wherein the information sent to the second node is a codec mode request or command, and wherein the current AMR source rate corresponds to a full rate AMR mode and the codec mode request or command corresponds to a half rate AMR mode.

8. The method in claim 7, further comprising:
   in response to the determined need, starting a timer set with a predetermined delay period, and
   after the timer expires, sending an indication the first node to start transmitting at the half rate data transmission rate over the radio interface.

9. The method in claim 8, wherein waiting for the predetermined delay period before performing the commanding step allows sufficient time for the second node to adjust from the full rate AMR mode to the half rate AMR mode so that the AMR source encoding rate of information sent to first node does not exceed the half rate data transmission rate over the radio interface.

10. The method in claim 7, further comprising:
    sending multiple codec mode request or commands to the second node to stepwise adjust from the full rate AMR mode down to the half rate AMR mode.

11. The method in claim 6, wherein the wireless communication system first node communicates over the radio interface using a first full rate radio channel and the commanding step includes a handover command to cause the first node to start transmitting at the second data transmission rate over a half rate radio channel, and wherein after the handover is performed, the second node's AMR encoder generates source data based on the new AMR source bit rate.

12. The method in claim 11, wherein by the time the handover is performed, the second node's AMR encoder is generating source data based on the new AMR source bit rate.

13. The method in claim 12, wherein the handover is orchestrated by a base station controller that controls one or more base stations involved in the handover.

14. The method in claim 12, wherein the handover is orchestrated by a a control node that controls two or more base stations controllers that each control one or more base stations involved in the handover.

15. The method in claim 1, further comprising:
    determining a round trip time associated with the communication between the first node and second node;
    determining the predetermined delay period based on the round trip time.

16. The method in claim 1, further comprising:
    sending information to the second node so that the second node changes from the current AMR source bit rate to the new AMR source bit rate in multiple steps.

17. Apparatus for controlling Adaptive Multi-Rate (AMR) encoding of speech signals that are to be sent between a first node and a second node in a wireless communication system, where an AMR encoder associated with each of the first node and the second node encodes speech signals in multiple modes having different degrees of robustness that correspond to different AMR source bit rates, where for a communication established between the first node and the second node, the first node transmits over a radio interface at a first data transmission rate, and where the AMR encoders associated with the first node and the second node generate source data for transmission at a first AMR source bit rate, the apparatus comprising electronic circuitry configured to:
    determine a need to change the first node's first data transmission rate over the radio interface to a second different data transmission rate;
    in response to the determined need, determine a new AMR source bit rate for the first node and the second node;
    in advance of changing the data transmission rate over the radio interface, provide information for transmission to the second node requesting the second node to change from the current AMR source bit rate towards the new AMR source bit rate; and
    after a predetermined time period sufficient for the second node to change from the current AMR source bit rate to the new AMR source bit rate expires or after the second node indicates a change to the new AMR source bit rate, provide for transmission to the first node an indication for the first node to start transmitting at the second data transmission rate over the radio interface.

18. The apparatus in claim 17, wherein waiting for the predetermined delay period allows sufficient time for the second node to adjust its AMR source encoding rate to the second AMR source encoding rate so that the AMR source encoding rate of information sent to first node is compatible with the second data transmission rate over the radio interface.

19. The apparatus in claim 17, wherein the electronic circuitry is configured to send the information to the second node using in-band signaling in a user plane.

20. The apparatus in claim 19, wherein the information sent to the second node is a codec mode request or command.

21. The apparatus in claim 17, wherein the electronic circuitry is configured to detect a condition that indicates a need to change the first node's first data transmission rate over the radio interface.

22. The apparatus in claim 21, wherein the wireless communication system is a GSM-based wireless communication system, the condition is a congestion condition, and the second data transmission rate corresponds to a half rate radio channel and the first data transmission rate corresponds to a full rate radio channel.

23. The apparatus in claim 22, wherein the information sent to the second node is a codec mode request or command, and wherein the current AMR source rate corresponds to a full rate AMR mode and the codec mode request or command corresponds to a half rate AMR mode.

24. The apparatus in claim 23, wherein the electronic circuitry is configured to:
    start a timer set with a predetermined delay period in response to the determined need, and
    provide for transmission to the first node an indication for the first node to start transmitting at the half rate data transmission rate over the radio interface after the timer expires.

25. The apparatus in claim 24, wherein waiting for the predetermined delay period allows sufficient time for the second node to adjust from the full rate AMR mode to the half rate AMR mode so that the AMR source encoding rate of information sent to first node does not exceed the half rate data transmission rate over the radio interface.

26. The apparatus in claim 24, wherein the electronic circuitry is configured to provide for transmission to the second node multiple codec mode request or commands for the second node to stepwise adjust from the full rate AMR mode down to the half rate AMR mode.

27. The apparatus in claim 24, wherein the first node communicates over the radio interface using a first full rate radio channel, and wherein the electronic circuitry is configured to provide a handover command to cause the first node to start transmitting at the second data transmission rate over a half rate radio channel such that after the handover is performed, the second node's AMR encoder generates source data based on the new AMR source bit rate.

28. The apparatus in claim 27, wherein by the time the handover is performed, the second node's AMR encoder is generating source data based on the new AMR source bit rate.

29. The apparatus in claim 28 implemented in a base station controller that controls one or more base stations involved in the handover.

30. The apparatus in claim 28 implemented in a control node that controls two or more base stations controllers that each control one or more base stations involved in the handover.

31. The apparatus in claim 17, wherein the electronic circuitry is configured to:
  determine a round trip time associated with the communication between the first node and second node;
  determine the predetermined delay period based on the round trip time.

32. The apparatus in claim 17, wherein the electronic circuitry is configured to send information to the second node so that the second node changes from the current AMR source bit rate to the new AMR source bit rate in multiple steps.

33. Apparatus for controlling Adaptive Multi-Rate (AMR) encoding of speech signals that are to be sent between a first node and a second node in a wireless communication system, where an AMR encoder associated with each of the first node and the second node encodes speech signals in multiple modes having different degrees of robustness that correspond to different AMR source bit rates, where for a communication established between the first node and the second node, the first node transmits over a radio interface at a first data transmission rate, and where the AMR encoders associated with the first node and the second node generate source data for transmission at a first AMR source bit rate, comprising:
  means for determining a need to change the first node's first data transmission rate over the radio interface to a second different data transmission rate;
  means, in response to the determined need, for determining a new AMR source bit rate for the first node and the second node;
  means for sending information to the second node, in advance of changing the data transmission rate over the radio interface, requesting the second node to change from the current AMR source bit rate towards the new AMR source bit rate; and
  means for sending an indication to the first node to start transmitting at the second data transmission rate over the radio interface after a predetermined time period sufficient for the second node to change from the current AMR source bit rate to the new AMR source bit rate expires or after the second node indicates a change to the new AMR source bit rate.

* * * * *

UNITED STATES PATENT AND TRADEMARK OFFICE
CERTIFICATE OF CORRECTION

PATENT NO. : 8,200,215 B2
APPLICATION NO. : 12/607404
DATED : June 12, 2012
INVENTOR(S) : Schliwa-Bertling et al.

It is certified that error appears in the above-identified patent and that said Letters Patent is hereby corrected as shown below:

In Fig. 4, Sheet 4 of 16, delete "Speech from MSA" and
insert -- Speech from MS A --, therefor.

In Fig. 5C, Sheet 6 of 16, delete "MS B from MSA" and
insert -- MS B from MS A --, therefor.

In Fig. 12, Sheet 14 of 16, below "Delay Timer expires", in Line 1, delete "Assigment" and
insert -- Assignment --, therefor.

In Fig. 12, Sheet 14 of 16, below "CMR stepwise to ICM", in Line 1,
delete "Assigment" and insert -- Assignment --, therefor.

In Fig. 12, Sheet 14 of 16, delete "Abis interace" and insert -- Abis interface --, therefor.

In Fig. 13, Sheet 15 of 16, delete "Abis interace" and insert -- Abis interface --, therefor.

In Fig. 14, Sheet 16 of 16, delete "Abis interace" and insert -- Abis interface --, therefor.

In Column 2, Line 20, delete "ins," and insert -- ms, --, therefor.

In Column 3, Line 38, delete "mode" and insert -- mode. --, therefor.

In Column 5, Line 49, delete "station." and insert -- station --, therefor.

In Column 6, Line 12, delete "a." and insert -- a --, therefor.

Signed and Sealed this
Thirteenth Day of November, 2012

David J. Kappos
*Director of the United States Patent and Trademark Office*

CERTIFICATE OF CORRECTION (continued)
U.S. Pat. No. 8,200,215 B2

In Column 8, Line 43, delete "122" and insert -- 12.2 --, therefor.

In Column 11, Line 50, in Claim 14, delete "a a" and insert -- a --, therefor.